US00PP32605P2

(12) United States Plant Patent
Griffin

(10) Patent No.: US PP32,605 P2
(45) Date of Patent: Dec. 8, 2020

(54) ***ALOE* PLANT 'PURPLE PEOPLE EATER'**

(50) Latin Name: ***Aloe* hybrid**
Varietal Denomination: PURPLE PEOPLE EATER

(71) Applicant: Altman Specialty Plants, Inc, Vista, CA (US)

(72) Inventor: Kelly Griffin, Carlsbad, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 16/873,349

(22) Filed: Mar. 24, 2020

(51) Int. Cl.
*A01H 5/00* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — Cassandra Bright

(57) ABSTRACT

A new and distinct cultivar of *Aloe* plant named 'PURPLE PEOPLE EATER' is disclosed, characterized by fringed leaves with micro serrations on star shaped plant. Plants produce dense lavender clustering rosettes, and red flowers. The new variety is an *Aloe*, typically produced as a garden or container plant.

1 Drawing Sheet

Latin name of the genus and species: *Aloe* hybrid.
Variety denomination: 'PURPLE PEOPLE EATER'.

BACKGROUND OF THE INVENTION

The new cultivar is a product of a planned breeding program. The seed parent is the unpatented *Aloe* 'Lavender Star'. The pollen parent is the unpatented *Aloe divaricata* x *Aloe intermedia*, x *Aloe acutissima*. The crossing was made in February 2016 at a commercial greenhouse in Vista, Calif. 'PURPLE PEOPLE EATER' was found and selected by the inventor in April 2017 at the same greenhouse in Vista, Calif.

Asexual reproduction of the new cultivar 'PURPLE PEOPLE EATER' was first performed by tissue culture at a commercial laboratory in Vista, Calif. in July 2017. 'PURPLE PEOPLE EATER' has since produced several generations and has shown that the unique features of this cultivar are stable and reproduced true to type.

SUMMARY OF THE INVENTION

The cultivar 'PURPLE PEOPLE EATER' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PURPLE PEOPLE EATER.' These characteristics in combination distinguish 'PURPLE PEOPLE EATER' as a new and distinct *Aloe* cultivar:

1. Compact plant forming clumps of up to thirty rosettes.
2. Glaucous lavender foliage with red dots and margins.
3. Vigorous growth
4. Observed disease and insect resistance.
5. Table top *Aloe*, clumping at maturity at 8" across.

PARENTAL COMPARISON

Plants of the new cultivar 'PURPLE PEOPLE EATER' are similar to the seed parent in most horticultural characteristics. However, plants of the new variety differ from the seed parent in the following:

1. The seed parent is less compact and does not clump like the new variety.
2. The new variety grows more vigorously than the seed parent.
4. The new variety is significantly more disease and insect resistant than the seed parent.

Plants of the new cultivar 'PURPLE PEOPLE EATER' are similar to the pollen parent in most horticultural characteristics. However, plants of the new variety differ in the following:

1. The new variety is a smaller plant than the pollen parent.
2. The new variety produces more clumps than the pollen parent.

COMMERCIAL COMPARISON

'PURPLE PEOPLE EATER' can be compared to the unpatented commercial variety *Aloe* 'Lavender Star'. The two *Aloe* varieties are similar in most horticultural characteristics; however, the new variety differs in the following:

1. Plants of the new variety are larger than this comparator.
2. The new variety has more colorful leaves than this comparator.
3. Leaves of the new variety have a brighter purple coloring in bright light levels than leaves of this comparator.
4. The new variety has a cleaner growth habit than this comparator.

BRIEF DESCRIPTION OF THE PHOTOGRAPHS

The accompanying photograph illustrates in full color a typical plant of 'PURPLE PEOPLE EATER' grown in a greenhouse in Vista, Calif. This plant is approximately 20 months old, shown in a 1-gallon container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2007 edition, except where general terms of ordinary dictionary significance are used. The following observations and measurements describe 'PURPLE PEOPLE EATER' plants in a commercial greenhouse in Vista, Calif. Temperatures ranged from 21° C. to 25° C. during the day, and 18° C. to 21° C. during the night. No artificial light, photoperiodic treatments or chemical treatments were given to the plants. Natural light conditions were approximately 2500 to 3000 fc of light. Measurements and numerical values represent averages of typical plant types.

Botanical classification: *Aloe* hybrid 'PURPLE PEOPLE EATER.'.

Age of the plant described: 2 years.

PROPAGATION

Time to initiate roots: Approximately 25 days at 22° C.

Root description: Fibrous. Brown, not accurately measured with The R.H.S. chart.

Propagation method: Tissue culture.

PLANT

Growth habit: Upright rosette, offsetting to form clumps with time.

Container size: 6 inches.

Height: Approximately 25 cm to top of highest leaf. Approximately 35 cm to top of highest inflorescence.

Plant spread: Approximately 35 cm.

Growth rate: Moderate.

Branching characteristics: Offsets to form clumps.

FOLIAGE

Leaf:

*Arrangement*.—Rosette.

*Average length*.—Average 14-16 cm.

*Average width*.—Average 3-4 cm.

*Shape of blade*.—Narrow deltoid.

*Apex*.—Acuminate.

*Base*.—Clasping.

*Margin*.—Flanged, colored edge.

*Texture of top surface*.—Prickles, bars and ribs.

*Texture of bottom surface*.—Bars and ribs.

*Quantity of leaves per plant*.—Average 10.

*Color*.—Young foliage upper side: Near RHS Greyed-Purple N187D. moderate elongated speckles, about 1 to 2 mm wide and 3 to 5 mm long colored near Red 46C. Margin colored near Red 46A. Young foliage under side: Near RHS Greyed-Purple N187D. moderate elongated speckles, about 1 to 2 mm wide and 3 to 5 mm long colored near Red 46D. Margin colored near Red 46A. Mature foliage upper side: Near RHS Greyed-Purple N187D. moderate elongated speckles, about 1 to 2 mm wide and 3 to 5 mm long colored near Red 46B. Margin colored near Red 46A. Mature foliage under side: Near RHS Greyed-Purple N187D. moderate elongated speckles, about 1 to 2 mm wide and 3 to 5 mm long colored near Red 46C. Margin colored near Red 46A.

*Venation*.—Linear. Color: Indistinguishable from leaf blade.

FLOWER

Natural flowering season: Rebloomer, three to four times a year.

Inflorescence type and habit: Panicle, seldom branched.

Rate of flower opening: Moderate, successive.

Flower longevity on plant: 1.5 months.

Quantity of flowers: 10 to 20.

Total inflorescence size:

*Height*.—Approximately 28 cm.

*Width*.—Approximately 8 cm.

Corolla:

*Arrangement*.—Perianth cylindrical/corolla small and reflexed.

*Length*.—Approximately 2.5 cm.

*Width*.—Approximately 1 cm at widest point.

*Color*.—Tepals: When opening: Outer surface: Near RHS Red 39A. Inner surface: Near RHS Yellow 13D. Fully opened: Outer surface: Near RHS Red 39A. Inner surface: Near RHS Yellow 13D.

Bud:

*Shape*.—Cylindrical.

*Length*.—Approximately 2.5 cm.

*Diameter*.—Approximately 0.5 cm.

*Color*.—Near RHS Red 39A.

Pedicels:

*Length*.—Approximately 1 cm.

*Width*.—0.02 cm.

*Aspect*.—Lateral.

*Color*.—Near RHS Red 39B.

Fragrance: None.

REPRODUCTIVE ORGANS

Stamens:

*Number*.—6.

*Filament length*.—Approximately 2.5 cm.

*Filament color*.—Near White N155C.

*Anther length*.—0.25 cm.

*Anther color*.—Near Yellow 10A.

*Anther shape*.—Oval.

*Pollen color*.—Near Yellow 13B.

Pistil:

*Number*.—1.

*Length*.—Approximately 3 cm.

*Style color*.—Near White N155C.

*Stigma*.—Shape: Rounded. Color: Near White N155C. Ovary color: Near RHS Green 138D.

OTHER CHARACTERISTICS

Seeds and fruits: Pods about 10 mm long and 5 mm wide, colored near Green 137D when immature, ripening to Grey-Brown N199D. Seed dust like, colored near Grey-Brown 199C.

Temperature tolerance: Tolerates temperatures from approximately 0° to at least 35° C.

Disease/pest resistance: Shows mite resistance and black spot resistance.

What is claimed is:

1. A new and distinct cultivar of *Aloe* plant named 'PURPLE PEOPLE EATER' as herein illustrated and described.

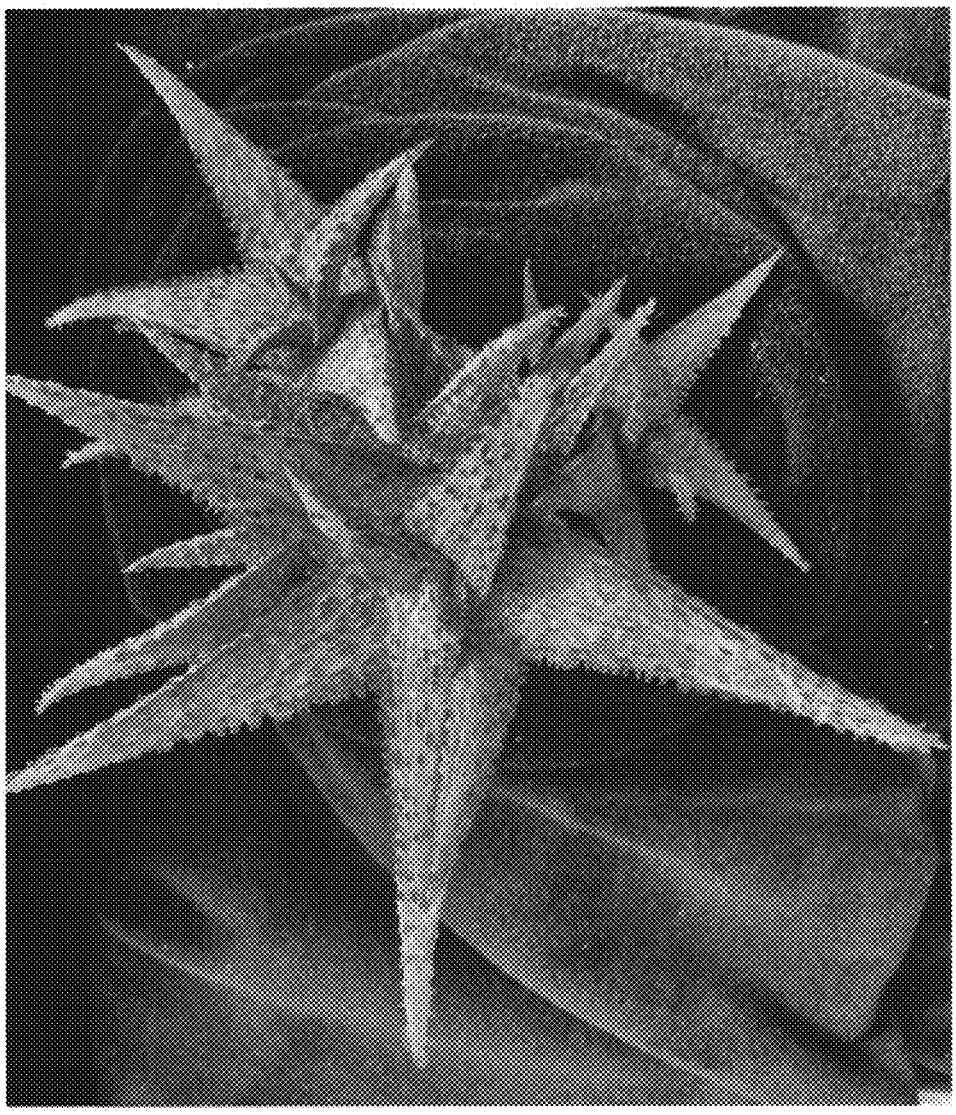

* * * * *